(12) United States Patent
Palmieri et al.

(10) Patent No.: US 8,083,916 B2
(45) Date of Patent: Dec. 27, 2011

(54) DETECTION DEVICE HAVING INCREASED DETECTION RATE, AND METHOD FOR QUICK DETECTION OF BIOLOGICAL MOLECULES

(75) Inventors: Michele Palmieri, Agrate Brianza (IT); Alessandra Fischetti, Milan (IT)

(73) Assignee: STMicroelectronics S.R.L., Agrate Brianza (IT)

( * ) Notice: Subject to any disclaimer, the term of this patent is extended or adjusted under 35 U.S.C. 154(b) by 1146 days.

(21) Appl. No.: 11/179,233

(22) Filed: Jul. 12, 2005

(65) Prior Publication Data
US 2006/0115828 A1    Jun. 1, 2006

(30) Foreign Application Priority Data
Jul. 19, 2004 (EP) .................... 04425535

(51) Int. Cl.
*B03C 5/02* (2006.01)
(52) U.S. Cl. ............ 204/547; 204/406
(58) Field of Classification Search .......... 435/287.2; 204/403.01, 406, 411, 643, 547
See application file for complete search history.

(56) References Cited

U.S. PATENT DOCUMENTS

| | | | |
|---|---|---|---|
| 5,429,734 A | 7/1995 | Gajar et al. | |
| 5,605,662 A * | 2/1997 | Heller et al. | 422/68.1 |
| 5,632,957 A * | 5/1997 | Heller et al. | 506/39 |
| 5,639,423 A | 6/1997 | Northrup et al. | |
| 5,942,443 A | 8/1999 | Parce et al. | |
| 6,001,229 A | 12/1999 | Ramsey | |
| 6,010,607 A | 1/2000 | Ramsey | |
| 6,010,608 A | 1/2000 | Ramsey | |
| 6,267,858 B1 | 7/2001 | Parce et al. | |
| 6,331,274 B1 * | 12/2001 | Ackley et al. | 422/68.1 |
| 6,518,022 B1 | 2/2003 | Sosnowski et al. | |
| 2002/0017660 A1 | 2/2002 | Villa et al. | |
| 2002/0045244 A1 | 4/2002 | Barlocchi et al. | |
| 2002/0068334 A1 | 6/2002 | Carrino et al. | |
| 2002/0068357 A1 | 6/2002 | Mathies et al. | |
| 2002/0097900 A1 | 7/2002 | Arena et al. | |
| 2003/0057199 A1 | 3/2003 | Villa et al. | |
| 2003/0146100 A1 * | 8/2003 | Huang et al. | 204/547 |
| 2004/0011650 A1 * | 1/2004 | Zenhausern et al. | 204/547 |

FOREIGN PATENT DOCUMENTS

| | | |
|---|---|---|
| EP | 1043770 A1 | 10/2000 |
| EP | 1049157 A1 | 11/2000 |
| EP | 1130631 A1 | 5/2001 |
| EP | 1123739 A1 | 8/2001 |
| WO | WO96/15576 | 5/1996 |
| WO | WO98/50773 | 6/1998 |

OTHER PUBLICATIONS

M. J. Heller, "An Active Microelectronics Device for Multiplex DNA Analysis", IEEE Engineering in Medicine and Biology, vol. 15, No. 2, Mar./Apr. 1996, p. 101-104.*

* cited by examiner

Primary Examiner — Jeffrey T Barton
Assistant Examiner — J. Christopher Ball
(74) Attorney, Agent, or Firm — Boulware & Valoir (57) ABSTRACT

A biological molecule detection device that includes a detection array, arranged on a body and having one or more probes for detecting corresponding electrically charged molecules, wherein a time varying electric field generating circuit is provided for generating at least one time varying electric field around the detection array within the detection region. The time varying electric field moves the electrical charged molecules repeatedly back and forth over the probes, thus providing increased opportunities for interaction and speeding the detection process.

5 Claims, 7 Drawing Sheets

DETECTION DEVICE HAVING INCREASED DETECTION RATE, AND METHOD FOR QUICK DETECTION OF BIOLOGICAL MOLECULES

CROSS-REFERENCE TO RELATED APPLICATIONS

This application claims priority to EP 04425535.4, filed Jul. 19, 2004, and is incorporated in its entirety herein by reference.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

The present invention relates to a biological molecules detection device having increased detection rate, and to a method for quick detection of biological molecules.

Typical procedures for analyzing biological materials, such as nucleic acid, involve a variety of operations starting from raw material. These operations may include various degrees of cell purification, lysis, amplification or purification, and analysis of the resulting amplified or purified product.

As an example, in DNA-based blood tests the samples are often purified by filtration, centrifugation or by electrophoresis so as to eliminate all the non-nucleated cells. Then, the remaining white blood cells are lysed using chemical, thermal or biochemical means in order to liberate the DNA to be analyzed.

Next, the DNA is denatured by thermal, biochemical or chemical processes and amplified by an amplification reaction, such as PCR (polymerase chain reaction), LCR (ligase chain reaction), SDA (strand displacement amplification), TMA (transcription-mediated amplification), RCA (rolling circle amplification), and the like. The amplification step allows the operator to avoid purification of the DNA being studied because the amplified product greatly exceeds the starting DNA in the sample.

The procedures are similar if RNA is to be analyzed, but more emphasis is placed on purification or other means to protect the labile RNA molecule. RNA is usually copied into DNA (cDNA) and then the analysis proceeds as described for DNA.

Finally, the amplification product undergoes some type of analysis, usually based on sequence or size or some combination thereof. In an analysis by hybridization, for example, the amplified DNA is passed over a plurality of detectors made up of individual oligonucleotide probe fragments (probes) that are anchored, for example, on electrodes. If the amplified DNA strands are complementary to the probes, stable bonds will be formed between them and the hybridized probes can be read by observation using a wide variety of means, including optical, electrical, mechanical, magnetic or thermal means.

Other biological molecules are analyzed in a similar way, but typically molecule purification is substituted for amplification and detection methods vary according to the molecule being detected. For example, a common diagnostic involves the detection of a specific protein by binding to its antibody or by a specific enzymatic reaction. Lipids, carbohydrates, drugs and small molecules from biological fluids are processed in similar ways.

In known microfluidic devices, the detectors are generally arranged in an array within a detection chamber. The probes are anchored in predetermined array locations to respective basements, which may be made either of conductive or insulating material. For example, the basements frequently comprise metal electrodes deposited on a bottom wall of the detection chamber. As an alternative, the probes are fixed to doped conductive regions in a semiconductor layer, such as a silicon substrate or an epitaxial layer. Moreover, conducting basements are often coated with a dielectric passivation layer for providing electrical insulation and protection against undesired chemical interactions between the electrodes and the biological sample in the detection chamber. Basements may be regions of a non-conducting material as well, such as silicon dioxide, silicon carbide, silicon nitride, undoped silicon, gels, polymers, and similar materials.

Several known techniques are used for anchoring the probes to the respective basements, such as spotting, chemical grafting, covalent binding, surface adsorption, or electrochemical methods.

The detection chambers presently exploited in microfluidic devices for biological analysis have some limitations. In order for hybridization to occur, for example, target DNA needs to be in the vicinity of its complementary probe. However, target DNA moves according to concentration gradients and random thermal motion. Hence, the DNA moves very slowly. Interactions between a probe and its corresponding target are accordingly quite unlikely and hybridization takes a very long time. Disadvantageously, the step of detection usually takes at least 20-30 minutes and, more frequently, about 1-2 hours or even more.

The aim of the present invention is to provide a detection device and method that are free from the above described drawbacks.

BRIEF SUMMARY OF THE INVENTION

According to the present invention a biological molecules detection device having increased detection rate, and a method for quick detection of biological molecules are provided, as defined in claims 1 and 13, respectively.

BRIEF SUMMARY OF THE DRAWINGS

For a better understanding of the present invention, some preferred embodiments thereof are now described, purely by way of non-limiting example, with reference to the attached drawings, in which.

DETAILED DESCRIPTION OF THE INVENTION

The discussion is herein simplified by focusing on nucleic acid analysis, in particular DNA amplification, as an example of a biological molecule that can be analyzed using the devices of the invention. However, as described above, the invention can be used for any chemical or biological test, wherein analyte molecules can be driven by electrical field, because they carry an electrical charge, or present a dielectric dipole, or are somehow polarized.

Generally speaking, the device contains controllable electrodes that surround the detectors. The method involves the generation of a pulsed voltage wave over the electrodes. A second pulsed wave travels at a different angle to the first wave. Additional waves may be used at a variety of angles, as desired. Using voltage waves that travel in different directions, the charged target molecules in the chamber are moved up and down, and back and forth across the detectors. Thus, there are greatly increased opportunities for the target molecules to interact with the arrayed probes and the speed of detection is tremendously increased.

Figure 1:
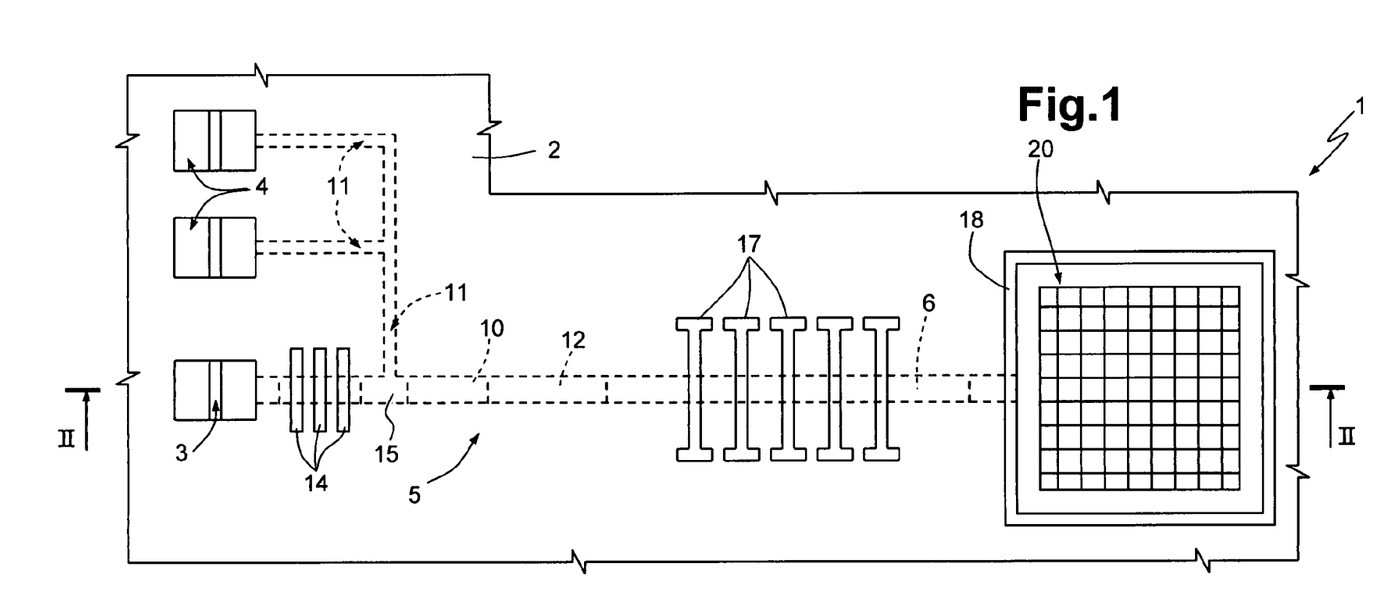
FIG. 1 is a top plan view of a microfluidic device integrating a detection device according to an embodiment of the invention.
Figure 2:
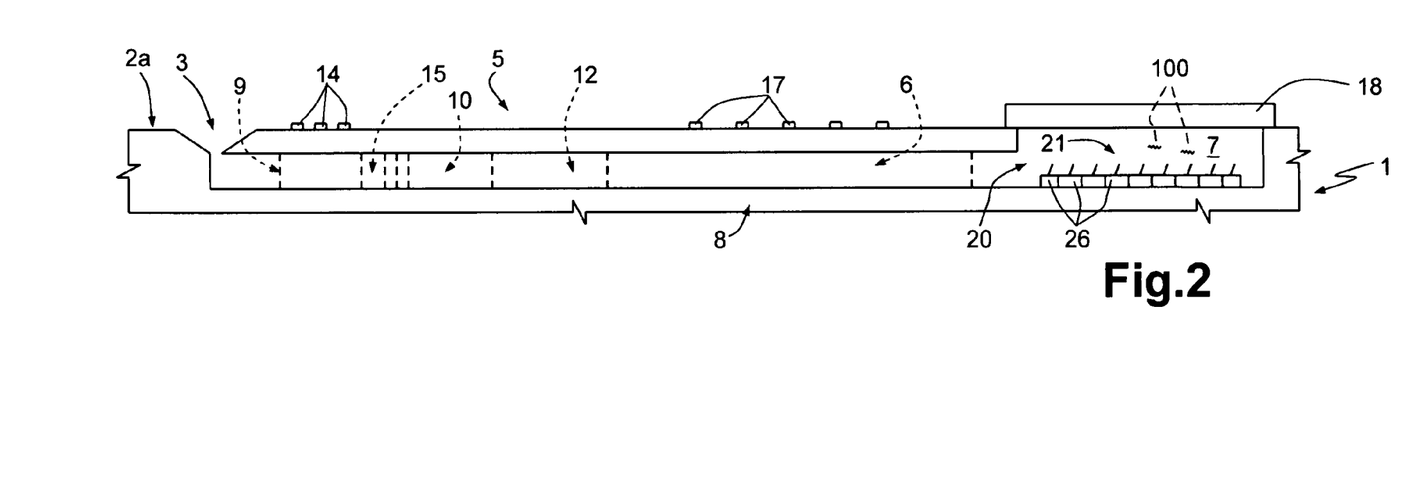
FIG. 2 is a sectional view through the microfluidic device of FIG. 1, taken along the line II-II of FIG. 1.

With reference to FIGS. 1 and 2, a microfluidic device 1, here a microreactor for nucleic acid analysis, is integrated in a monolithic semiconductor body 2, preferably P type silicon. The microfluidic device 1 comprises a sample reservoir 3, reagents reservoirs 4, a sample preparation channel 5, for preparation of a raw biological sample provided in the sample reservoir 3, an amplification chamber 6, for amplifying nucleic acid sequences, for example by PCR, and a detection chamber 7, all of which are in mutual fluidic connection. According to the foregoing definition, "chamber" herein designates a region of the microfluidic device 1 where one step of the process takes place. A chamber may also comprise a section of a microfluidic channel. In particular, in the embodiment herein described the sample preparation channel 5 and the amplification chamber 6 are formed in respective portions of a microfluidic channel 8, which is buried in the semiconductor body 2 and has a rectangular or triangular cross-section.

The microfluidic device 1 is also provided with a micropump (not shown), for moving the biological material sample and reagents from the reservoirs 3, 4 toward the detection chamber 7, which is arranged downstream.

The sample reservoir 3 and the reagent reservoirs 4 are opened on a surface of the semiconductor body 2, so as to be accessible from the outside. These reservoirs 3, 4 function to supply the biological sample and the reagents required for the process carried out by the microfluidic device 1.

The sample preparation channel 5 comprises a dielectrophoretic cell 9, a mixer 10, fluidly coupled to the reagent reservoirs 4 through supply channels 11, and a lysis chamber 12, for chemical lysis of the nuclei of the cells contained in the biological sample.

In greater detail, dielectrophoresis electrodes 14 are arranged on the surface of the semiconductor body 2 transversally to the dielectrophoretic cell 9, so as to form a grid. Thus, in the dielectrophoretic cell 9 nucleated cells of the biological material sample may be separated from non-nucleated cells by applying a pulsed electric field. Moreover, the non-nucleated cells are filtered out.

The mixer 10 is arranged immediately downstream of a confluence region 15 of the supply channels 11 and favors mixing of the biological sample with reagents from the reagent reservoirs 4.

The amplification chamber 6 is located downstream of the lysis chamber 12 and is provided with heaters 17, arranged on the surface of the semiconductor body 2. The heaters are driven by a control unit, per se known and here not shown, in order to heat and cool the amplification chamber 6 and the substances contained therein according to a predetermined temperature profile.

The detection chamber 7 is flush with the surface of the semiconductor body 2, and is upwardly closed by a transparent plate 18 (e.g. a glass sheet), bonded on the semiconductor body 2. The detection chamber 7 accommodates a detection device 20, for detecting biological molecules, in particular target DNA 100.

In order to perform a nucleic acid analysis, a sample of raw biological material (e.g. blood) is introduced in the sample reservoir 3, as previously mentioned, and is moved to the sample preparation channel 5. After separation of nucleated cells (white blood cells, in this case) in the dielectrophoretic cell 9, the biological material is combined with reagents for the lysis and PCR processes, which are supplied by the reagent reservoirs 4. Then, the biological sample and the reagents are mixed in the static mixer 10 and moved to the lysis chamber 12, where the nuclei of the cells are chemically broken and the nucleic acid (DNA) is extracted. The DNA is thermally denatured and amplified in the amplification chamber 6 and, finally, the processed biological sample is supplied to the detection chamber 7, for hybridization of target nucleotide sequences and optical detection thereof.

Figure 3:
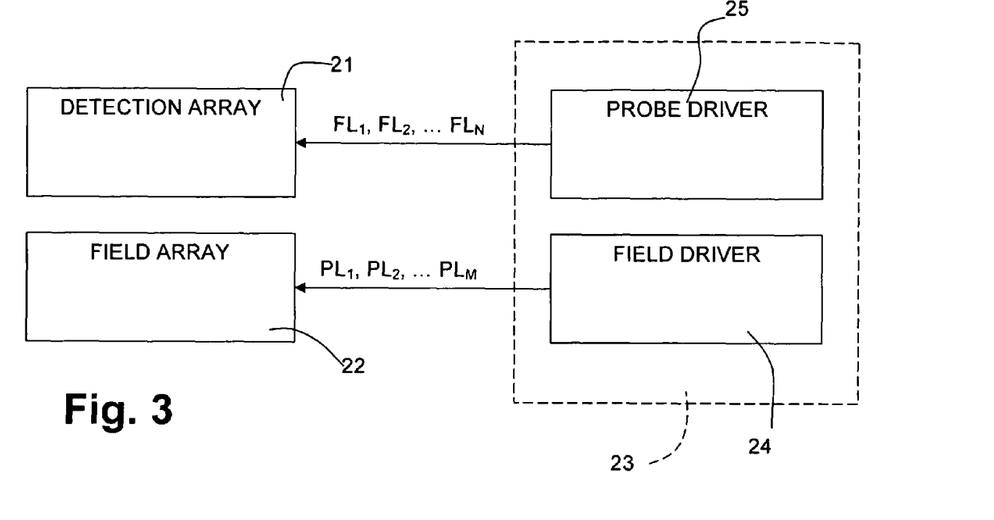
FIG. 3 is a simplified block diagram of the detection device of FIG. 1.
Figure 4:
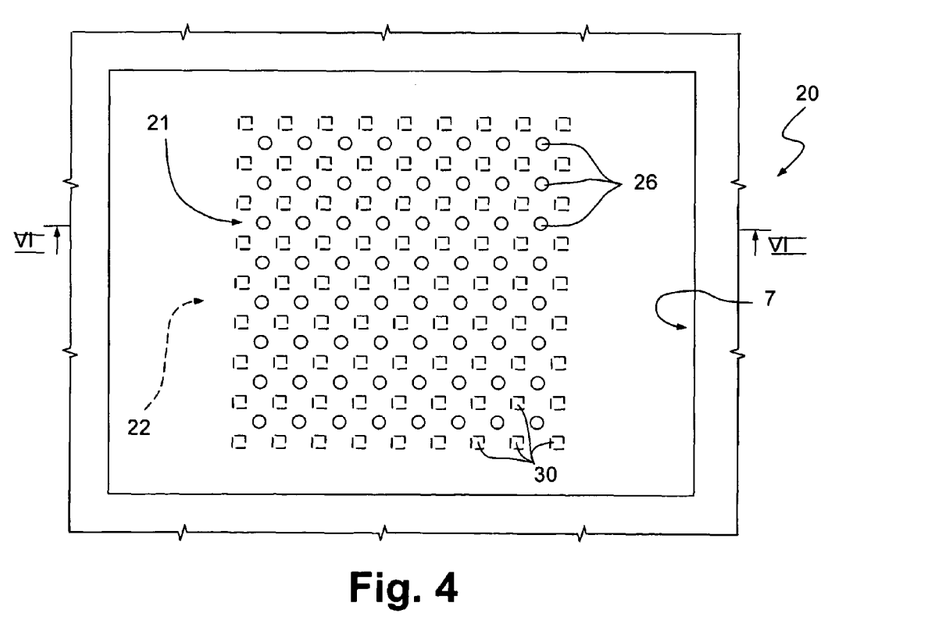
FIG. 4 is an enlarged top plan view of the detection device of FIG. 1.
Figure 5:
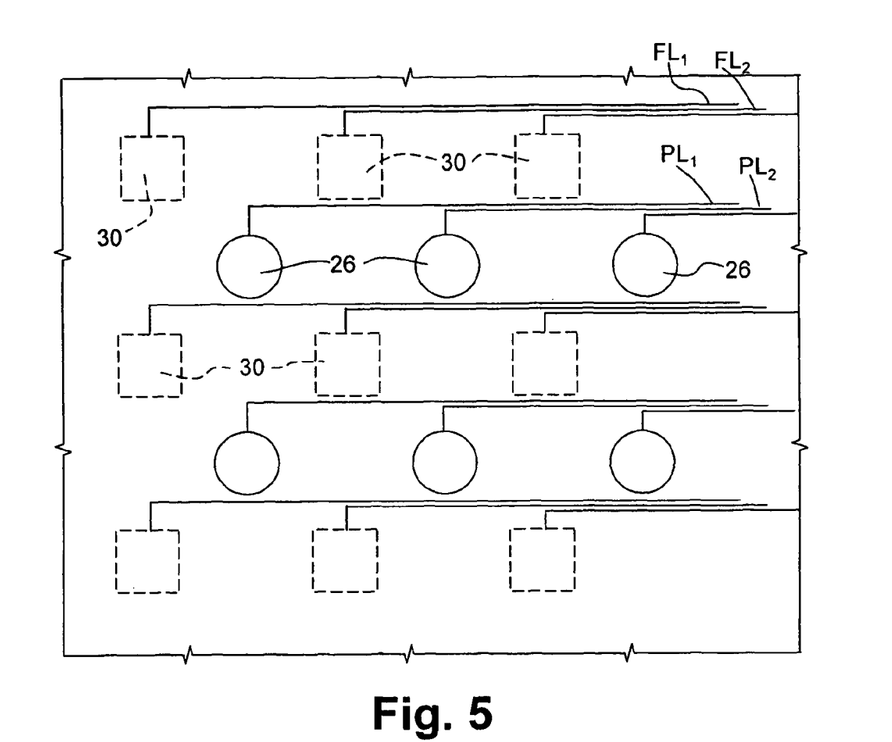
FIG. 5 is an enlarged view of a detail of FIG. 4.
Figure 6:
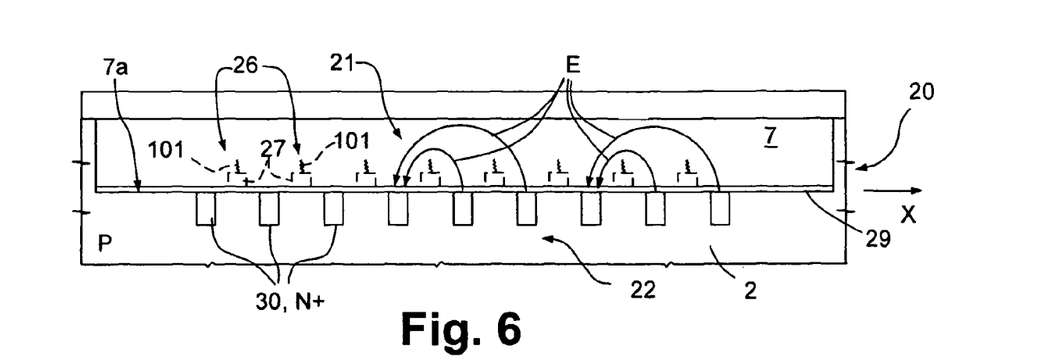
FIG. 6 is a sectional view through the detection device of FIG. 1, taken along the line VI-VI of FIG. 4.
Figure 7:
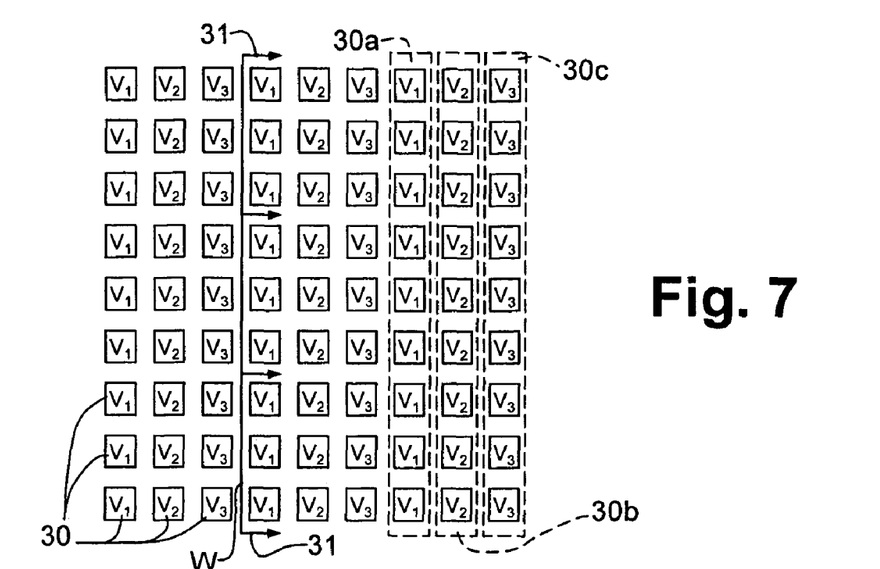
FIGS. 7-9 schematically illustrate successive operation steps of the detection device of FIG. 1, according to an embodiment of the invention.
Figure 8:
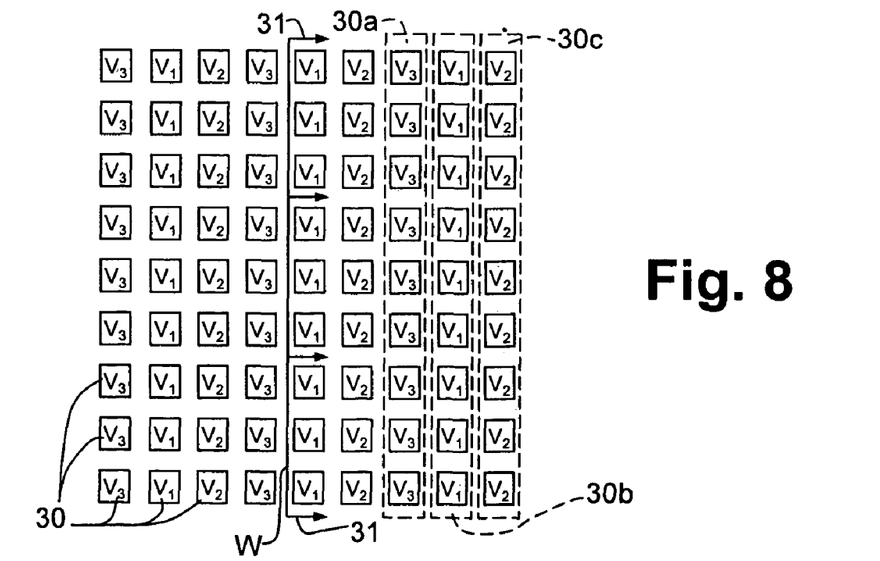
Figure 9:
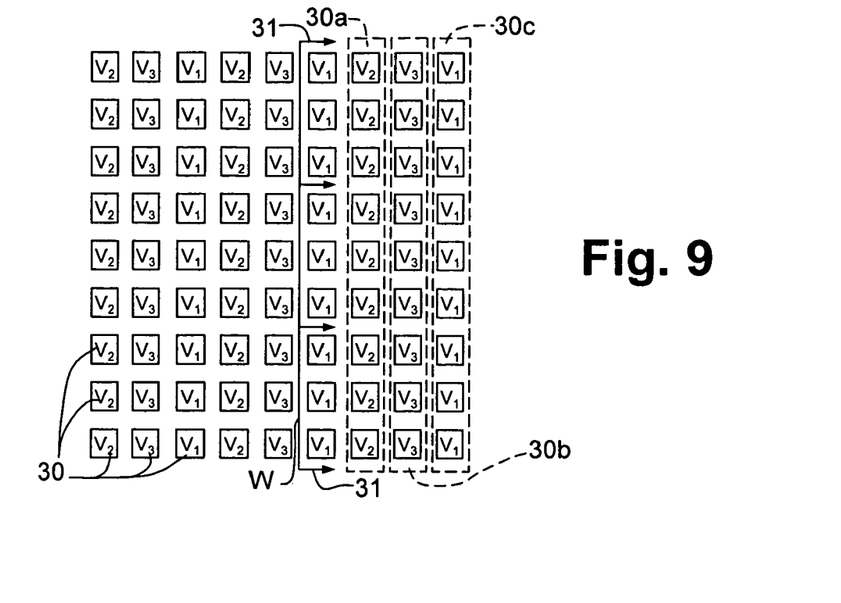
Figure 10:
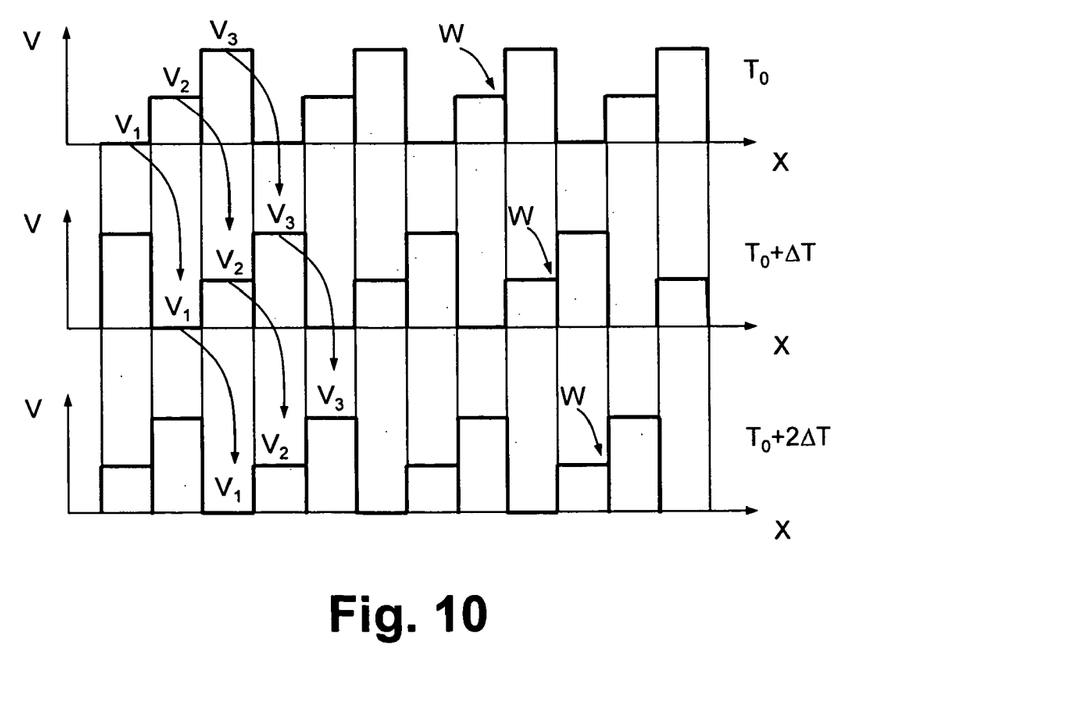
FIG. 10 is a graph showing plots of bias voltages relating to the detection device of FIG. 1.

FIG. 3 schematically shows the detection device 20, which comprises a detection array 21, a field array 22, and a control unit 23, including a probe driver circuit 25 and a field driver circuit 24. As illustrated in FIGS. 4-6, the detection array 21 comprises a plurality of probes 26 for DNA detection by hybridization, which are arranged in rows and columns and are per se known.

Each of the probes 26 has a respective probe electrode 27, forming a basement, and a number of respective molecules (e.g. 1 to 1000 molecules/$\mu m^2$) of probe DNA 101, anchored to the probe electrode 27 (FIG. 6). The probe electrodes 27 are formed on a dielectric layer 29 deposited on a bottom wall 7a of the detection chamber 7 (FIG. 6) and are preferably coated with a known passivation layer (not shown). The probe electrodes 27 are moreover coupled to the probe driver circuit 25 over respective probe connection lines $PL_1, PL_2, \ldots, PL_M$ (M being the total number of probes 26 in the detection device 20).

In order to favor selective anchoring of probe DNA 101 to respective probe electrodes 27 during a preliminary featuring step, the probe driver circuit 25 is configured for selectively activating one of the probe electrodes 27 by supplying a selection voltage, whereas all of the other probe electrodes 27 receive a deselection voltage and are deactivated.

The field array 22 comprises a plurality of N type conductive regions, which will be hereinafter referred to as field electrodes 30 (FIG. 4-6). The field electrodes 30, here of N+ type, are diffused within the semiconductor body 2 and are so arranged as to be interleaved with the probes 26 both by rows and columns. However, the field electrodes might be differently arranged and a predetermined topological correlation with the probe electrodes is not necessary.

In the embodiment herein described, each of the probes 26 is enclosed within four adjacent field electrodes 30. Each of the field electrodes 30 is coupled to the field driver circuit 24 over a respective field connection line $FL_1, FL_2, \ldots, FL_N$ (N being the total number of field electrodes 30).

As explained later on, the field driver circuit 24 addresses groups of field electrodes 30 and simultaneously provides different bias voltages to separate addressed groups. Moreover, each addressed group of field electrodes 30 periodically receives different bias voltages in successive driving steps.

In the examples illustrated in FIGS. 7-11, the field driver circuit 24 provides at least a first bias voltage $V_1$ (e.g. 0 V), a second bias voltage $V_2$, higher than the first bias voltage $V_1$ (e.g. 5 V), and a third bias voltage $V_3$ (e.g. 10 V), higher than the second bias voltage $V_2$. The field driver circuit 24 is also configured for modifying the groups of field electrodes 30 which are addressed in successive driving steps, and the sequence for supplying the bias voltages $V_1, V_2, V_3$.

Hence, the periodical and orderly biasing of the groups of field electrodes 30 causes voltage waves W and a non-uniform, time varying, traveling electric field E within the detecting chamber 7, in particular around the detection array 21 (see also FIG. 6). "Time varying" is herein used to indicate a dynamic electric field, which may be generated by either pulsed or continuously varying voltages, as opposed to a sequence of static electric field configurations. More specifically, the dynamic electric field varies so rapidly that the charged particles in the detection chamber 7 are at any time prevented from reaching a substantially steady configuration, and, in particular, from concentrating around a single probe 26 or probe electrode 27, contrary to the featuring step (as above explained, in the featuring step probe electrodes 27 are selectively and sequentially activated, in order to favor selective anchoring of probe DNA 101 to respective probe electrodes 27).

In the example illustrated in FIGS. 7-12, the field driver circuit 24 addresses three groups 30a, 30b, 30c of field electrodes 30 at a time. During a first driving step, which FIGS. 7-9 refer to, in each selected group 30a, 30b, 30c there is one column of field electrodes 30 every three. Accordingly, one column of field electrodes 30 every three (group 30b) receives the second bias voltage $V_2$, the next adjacent columns on the left (looking at FIG. 7, group 30a) receive the first bias voltage $V_1$, and the next adjacent columns on the right (group 30c) receive the third bias voltage $V_3$. Moreover, each group 30a, 30b, 30c of field electrodes 30 sequentially receives the third, the second and the first bias voltage $V_3, V_2, V_1$. The voltage waves W travel through the detecting chamber 7 in the direction indicated by arrows 31 in FIGS. 7-9, and their fronts are parallel to the columns of the field array 22. On account of the asymmetric distribution of the bias voltages $V_3, V_2, V_1$, also the voltage waves W are asymmetric in a direction X perpendicular to their fronts (see FIG. 10, which schematically illustrates the voltage distribution in the direction X at subsequent times $T_0, T_0+\Delta T, T_0+2\Delta T$).

Figure 11:
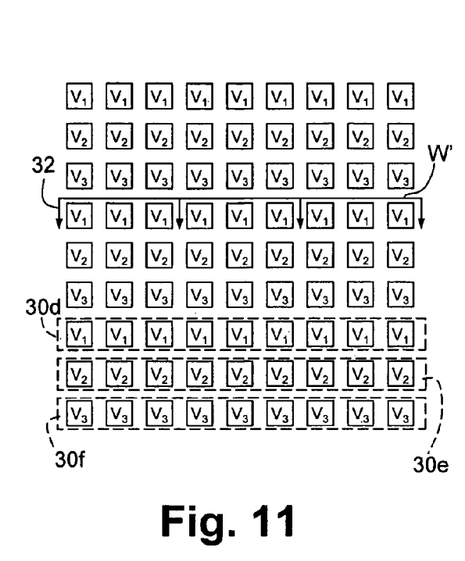
FIGS. 11 and 12 schematically illustrate further operation steps of the detection device of FIG. 1.
Figure 12:
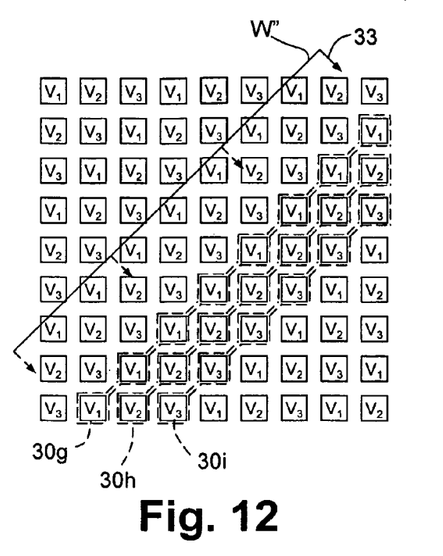

During a second driving step, the field driver circuit 24 addresses three groups 30d, 30e, 30f of field electrodes 30, different to the groups 30a, 30b, 30c previously addressed. Each of the groups 30d, 30e, 30f addressed by the field driver circuit 24 comprises one row of field electrodes 30 every three, as shown in FIG. 11. In this case, voltage waves W' travel through the detection chamber 7 in the direction indicated by arrows 32 and their fronts are parallel to the rows of the field array 22.

In a third driving step (FIG. 12), the field driver circuit 24 addresses three groups 30g, 30h, 30i of field electrodes 30, different to the groups 30a-30f previously addressed. In this case, the field electrodes 30 are addressed by the field driver circuit 24 according to diagonal lines of the field array 22, so that each group 30g, 30h, 30i comprises one diagonal line every three. Hence, voltage waves W" travel through the detection chamber 7 in the direction indicated by arrows 33 and their fronts are diagonal as well.

Preferably, the first, second and third driving step are cyclically repeated.

The time varying voltage distribution and electric field E continuously move the electrically charged molecules of the biological sample provided in the detection chamber 7. In particular, the target DNA 100 is negatively charged, so that the DNA tends to migrate toward those field electrodes 30 which are biased at the highest voltage, i.e. the third bias voltage $V_3$. However, the bias conditions of the field electrodes 30 rapidly vary, and static concentration of target DNA 100 is prevented. More precisely, target DNA 100 is transported through the detection chamber 7 according to the fronts of the voltage waves W, W', W", hence in several and variable directions. In practice, the average mobility of the target DNA 100 is significantly increased, so that interactions with probe DNA 101 grafted on the probe electrodes 27 are much more likely. In particular, the likelihood of undergoing interactions is raised for all the probes 26 simultaneously. Therefore, the hybridization rate of the probes 26 is increased and the overall detection time is correspondingly reduced. Less than one minute is required for complete hybridization of the probes 26 to their corresponding target DNAs 100.

Figure 13:
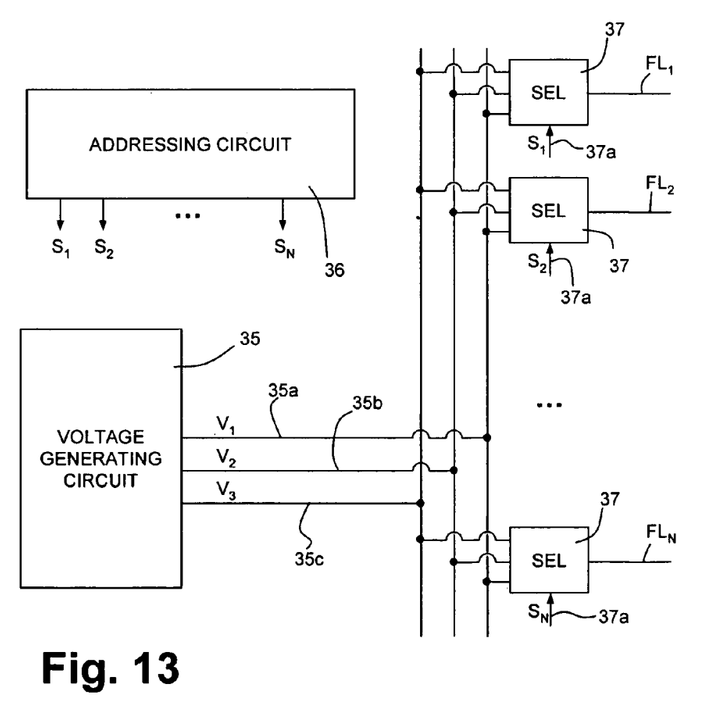
FIG. 13 is a more detailed diagram of a block of FIG. 3.

An example of field driver circuit 24 will be now described with reference to FIG. 13. The field driver circuit 24 comprises a voltage generating circuit 35, an addressing circuit 36, supplying a plurality of addressing signals $S_1, S_2, \ldots, S_N$, and a plurality of selectors 37, each of which is connected to a respective field electrode 30 (here not shown) over the corresponding field connection line $FL_1, FL_2, \ldots, FL_N$. The voltage generating circuit 35 has first, second and third output terminals 35a, 35b, 35c, respectively supplying the first, the second and the third bias voltage $V_1, V_2, V_3$. Each of the selectors 37 has three input terminals, respectively connected to the first, the second and the third output terminal 35a, 35b, 35c of the voltage generating circuit 35, and a control terminal 37a coupled to the addressing circuit 36 for receiving a respective addressing signal $S_1, S_2, \ldots, S_N$.

In particular, the addressing signals $S_1, S_2, \ldots, S_N$ have at least three logic levels: depending on the logic level of the addressing signal $S_1, S_2, \ldots, S_N$ supplied to the corresponding selector 37, each field connection line $FL_1, FL_2, \ldots, FL_N$ is selectively connected to the first, the second or the third output terminal 35a, 35b, 35c of the voltage generating circuit 35, for respectively receiving the first, the second or the third bias voltage $V_1, V_2, V_3$. Preferably, the addressing circuit 36 is programmable, so that the addressing signal $S_1, S_2, \ldots, S_N$ may be generated to provide the above described voltage distribution, or any other suitable voltage distribution.

The invention provides the following advantages. First, the hybridization rate is increased, by increasing the average mobility of the target DNA 100 and the likelihood of interaction with the probe DNA 101. Accordingly, simultaneous hybridization of the probes 26 is favored and the overall time required for analyzing a sample is greatly reduced. Second, the device and method described are very flexible, since a large variety of voltage distributions and traveling electric fields may be easily obtained. Moreover, the invention may be advantageously exploited irrespective of whether the basements for grafting the probe DNA 101 are conductive or not. Additionally, the detection device according to the invention is fully compatible with the fabrication of microfluidic devices incorporating buried channels.

Figure 14:
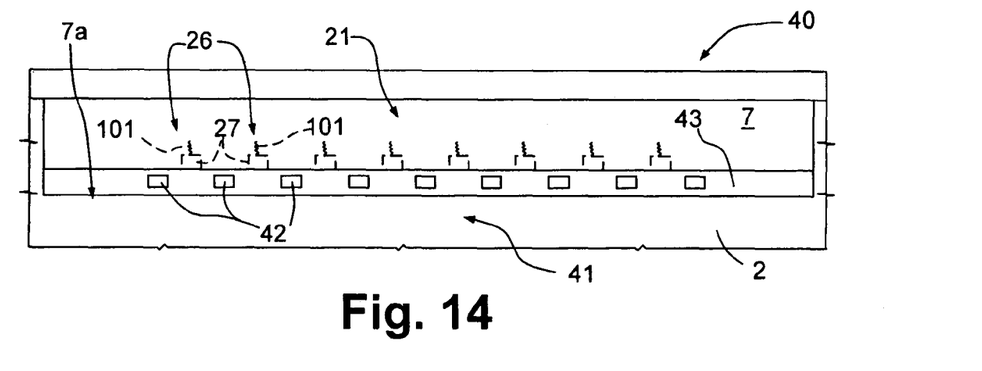
FIG. 14 is a cross sectional view through a detection device according to another embodiment of the invention.

According to a second embodiment of the invention, illustrated in FIG. 14, a detecting device 40 comprises the detection array 21, a field array 41, the probe driver circuit 25 and field driver circuit 24 (here not shown). The detection array 21 is arranged on a dielectric layer 43, which is in turn deposited on the bottom wall 7a of the detection chamber 7. The field array 41 comprises a plurality of metal field electrodes 42, which are embedded in the dielectric layer 43. Also in this case, the field electrodes 42 are preferably interleaved with the probes 26, both by rows and columns.

Figure 15:
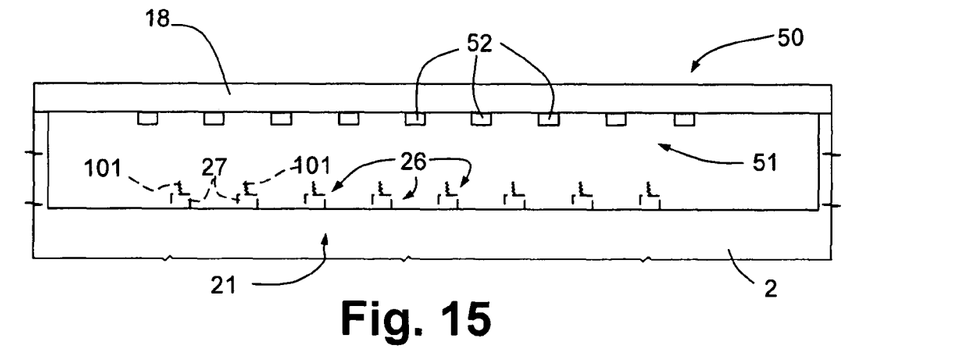
FIG. 15 is a cross sectional view through a detection device according to another embodiment of the invention.

A third embodiment of the invention is illustrated in FIG. 15. In particular, a detecting device 50, instead of being monolithically integrated with the semiconductor body 2, comprises a field array 51 of metal field electrodes 52, which are formed on the transparent plate 18. In particular, the metal field electrodes 52 are carried on a surface on the transparent plate 18, which upwardly delimits the detection chamber 7. In practice, the field array 51 is separately manufactured and is assembled to the semiconductor body 2, which accommodates the detection array 21, the probe driver circuit 25 and the field driver circuit 24 (not shown), by bonding the transparent plate 18. Hence, fabrication of the detecting device is simplified.

Figure 16:
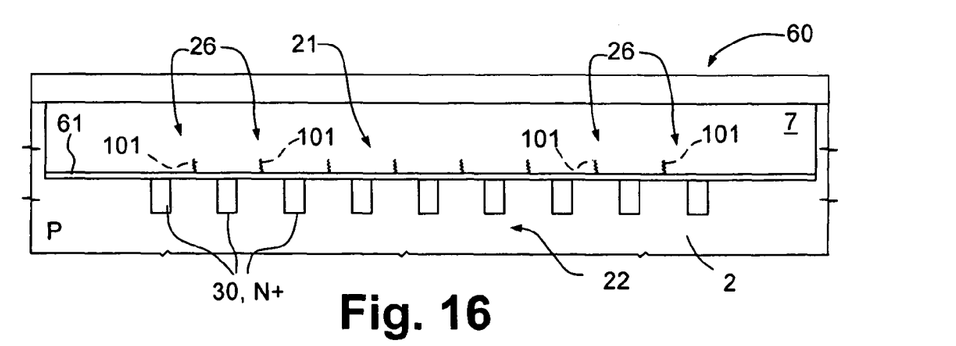
FIG. 16 is a cross sectional view through a detection device according to another embodiment of the invention.

According to a fourth embodiment of the invention shown in FIG. 16, in a detecting device 60 the probes 26 include probe DNA 101, which is directly anchored to a common dielectric basement layer 61 covering the field electrodes 30 of the field array 22. In this case, the probe electrodes 27 and the probe driver circuit 25 are not present.

Finally, it is clear that numerous modifications and variations may be made to the detection device and to method described and illustrated herein, all falling within the scope of the invention, as defined in the attached claims. In particular, the configuration of the field array and of the field driver circuit may be such as to provide any desired voltage distribution and electric field within the detection chamber. The field driver circuit may provide any suitable number of bias voltages (i.e. more than three) in any desired direction. For example, bias voltages need not be periodically repeated, but may be generated according to any predetermined sequence. Also AC bias voltages may be supplied to the field electrodes, instead of pulse-like voltages. In this case, bias voltages of adjacent field electrodes have predetermined phase-shift (e.g. of 180°, so that a stationary alternating electric field is provided). The field electrodes may also be different as to number, shape, location and distribution.

What is claimed is:

1. A method of performing a biological test, wherein a biological fluid is applied to a microfluidic device, comprising a semiconductor body having a detection chamber said detection chamber having a probe to detect electrically charged molecules, and a time varying electric field generating circuit having a plurality of electrodes, separate from and surrounding said probe, and a driving circuit coupled to said plurality of electrodes, to provide respective bias voltages to said electrodes generating a plurality of time varying non-uniform voltage waves in sequential variable, non-parallel directions to dynamically move said electrically charged molecules within said detection region, so that the electrically charged molecules are prevented from reaching a substantially steady configuration within said detection region, and a charged biological molecule is detected on said probe.

2. The method of claim 1, wherein the charged biological molecule is DNA.

3. A method for detection of charged molecules, comprising
   a) introducing a sample containing electrically charged molecules into a microfluidic detection device,
      said microfluidic detection device comprising a detection region having a plurality of probes to detect a plurality of electrically charged molecules and a time varying electric field generating circuit;
   b) generating a plurality of time varying non-uniform electric fields in sequential variable, non-parallel directions with said time varying electric field generating circuit so as to cause said plurality of electrically charged molecules to dynamically move within said detection region, so that the electrically charged molecules are prevented from reaching a substantially steady configuration within said detection region; and
   c) detecting the plurality of electrically charged molecules bound to said plurality of probes.

4. The method of claim 3, wherein said step of generating a time varying electric field comprises:
   a) arranging a plurality of probes and a plurality of first electrodes separate from and interleaved with said probes; and
   b) simultaneously providing respective bias voltages to separate groups of said first electrodes.

5. The method of claim 4, wherein said time varying non-uniform electric field is a periodic electric field.

* * * * *

UNITED STATES PATENT AND TRADEMARK OFFICE
CERTIFICATE OF CORRECTION

| | | |
|---|---|---|
| PATENT NO. | : 8,083,916 B2 | Page 1 of 1 |
| APPLICATION NO. | : 11/179233 | |
| DATED | : December 27, 2011 | |
| INVENTOR(S) | : Michele Palmieri and Alessandra Fischetti | |

It is certified that error appears in the above-identified patent and that said Letters Patent is hereby corrected as shown below:

IN THE CLAIMS:

Column 8, Line 4, Claim 1, should read as follows:

1. A method of performing a biological test, wherein a biological fluid is applied to a microfluidic device, comprising a semiconductor body having a detection chamber,     said detection chamber having a probe to detect electrically charged molecules, and     a time varying electric field generating circuit having         a plurality of electrodes, separate from and surrounding said probe, and         a driving circuit coupled to said plurality of electrodes, to provide respective bias voltages to said electrodes generating a plurality of time varying non-uniform voltage waves in sequential variable, non-parallel directions to dynamically move said electrically charged molecules within said detection region, so that the electrically charged molecules are prevented from reaching a substantially steady configuration within said detection region, and     a charged biological molecule is detected on said probe.

Signed and Sealed this
Fourteenth Day of February, 2012

David J. Kappos
*Director of the United States Patent and Trademark Office*